United States Patent [19]
Roy et al.

[11] Patent Number: 5,833,995
[45] Date of Patent: Nov. 10, 1998

[54] USE OF BLUETONGUE VIRUS PROTEINS AS VACCINE COMPONENTS

[75] Inventors: Polly Roy; Timothy J. French, both of Oxford, England

[73] Assignees: Oravax, Inc., Cambridge, Mass.; Natural Environmental Research Council, Swindon, England

[21] Appl. No.: 291,915

[22] Filed: Aug. 18, 1994

Related U.S. Application Data

[63] Continuation of Ser. No. 135,123, Sep. 22, 1993, abandoned, which is a continuation of Ser. No. 853,696, filed as PCT/GB90/01047, Jul. 6, 1990 published as WO91/00741 Jan. 25, 1991, abandoned.

[30] Foreign Application Priority Data

Jul. 7, 1989 [GB] United Kingdom ............... 8915572

[51] Int. Cl.$^6$ .......................... A61K 39/15; C12N 15/46; C07H 21/04
[52] U.S. Cl. ..................... 424/215.1; 424/215.1; 435/320.1; 514/44; 536/23.72
[58] Field of Search ............... 424/185.1, 186.1, 424/199.1, 204.1, 215.1; 514/2; 435/69.3, 172.3; 530/350, 826; 536/23.72

[56] References Cited

PUBLICATIONS

Ellism, RW. "New Technologies for Making Vaccines" In: Vaccines, Plotkin & Mortimer Eds, W.B. Saunders Co. 1988 pp. 568–575.
Huismans, H. et al. 1983. In: Double–Stranded RNA Viruses. Compans & Bishop. Ed. pp. 165–172.
Buzofsky, J.A. et al. 1985 Science 229: 932–940.
Luckow, V.A. et al. 1988. Bio/Technology 6: 47–55.
Inumaru, S. et al. 1987. Virology 157: 472–479.
Purdy, M.A. et al. 1986 J. Gen. Virol. 67: 957–962.
Huismans et al. "The Biochemical and Immunological Characterization of Bluetongue Virus Outer Capsid Polypeptides" Double–Stranded RNA Viruses, 1983, pp. 165–172.

*Primary Examiner*—Christine M. Nucker
*Assistant Examiner*—Phuong T. Bui
*Attorney, Agent, or Firm*—Nixon & Vanderhye

[57] ABSTRACT

A protective effect against bluetongue infection in susceptible mammals which is obtained by innoculating said mammals with a polypeptide comprising at least an antigenic portion of bluetongue virus structural protein VP2 in antigenic form produced by transforming a host with a recombinant expression vector having a DNA segment coding for said polypeptide.

5 Claims, 13 Drawing Sheets

FIG. 2 pAcYM1         -GTAATAAAAAACCCTATAAATACGGATCCGGTTATT-
                                  BamHI pAcYM1/10-5    -GTAATAAAAAACCCTATAAATACGGATCCGGTTAAAAAGTGTTCTCCTACTCGCAGAAG ATG GGGAA-
                                  BamHI                                           ────────▶
                                                                                  BTV-10 segment 5 pAcYM1/10-5    -ACGAAATGCT TGA ACGCGGATCCGGTTATT-
                          ◀────────        BamHI
                          BTV-10 segment 5 pAcYM1/10-2    -GTAATAAAAAACCCTATAAATACGGATCGGGGTTAAAAGAGTGTTCTACC ATG GAGAA-
                                                          tail    ────────▶
                                                                  BTV-10 segment 2

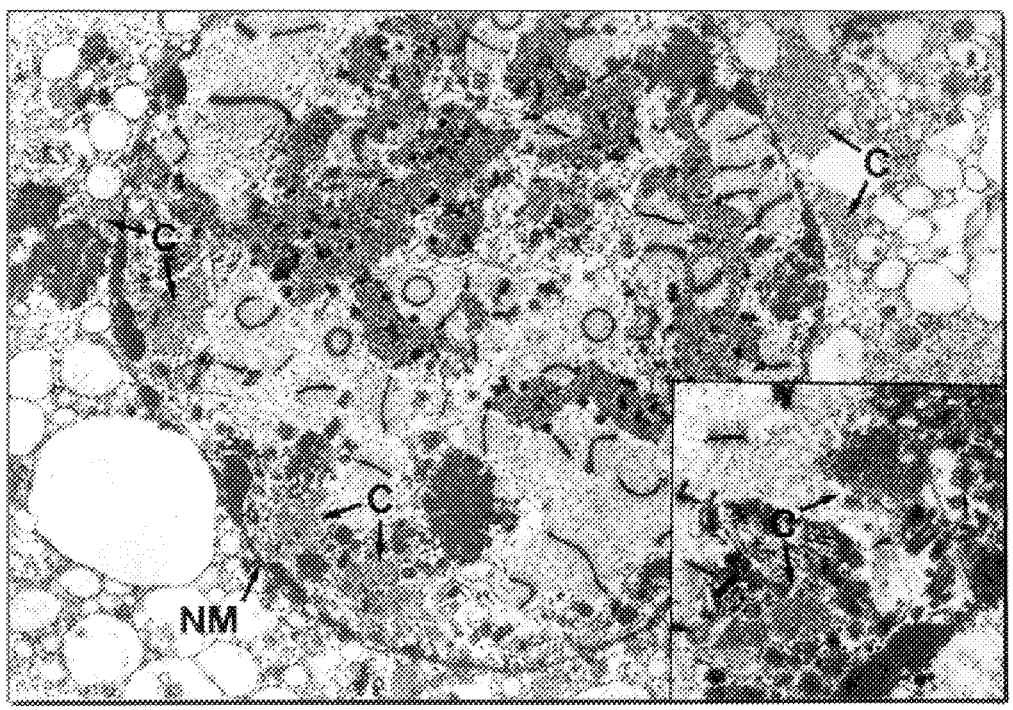

USE OF BLUETONGUE VIRUS PROTEINS AS VACCINE COMPONENTS

This is a continuation of application Ser. No. 08/135,123, filed 22 Sep. 1993, now abandoned, which is a continuation of application Ser. No. 07/853,696, filed as PCT/GB90/01047, Jul. 6, 1990 published as WO91/00741 Jan. 25, 1991, now abandoned.

This invention relates to use of bluetongue virus proteins as vaccine components.

BACKGROUND OF THE INVENTION

Bluetongue virus (BTV) is the prototype virus of the Orbivirus genus (Reoviridae family). It is vectored to vertebrates by Culicoides species and causes disease in certain ruminants, notably sheep.

The genome consists of ten double-stranded RNA segments, each of which is monocistronic, and is located in the core of the virion. The icosahedral core contains two major (VP3 and VP7) and three minor protein species (VP1, VP4, VP6) and is surrounded by a diffuse coat of the proteins VP2 and VP5 (Verwoerd et at., 1972) which are coded for by the RNA segments L2 and M5 respectively (Mertens et al., 1984). It is known that VP2 is the main serotype specific antigen (Huismans and Erasmus, 1981; Kahlon et al., 1983).

The genome of BTV consists of 10 unique double-stranded (ds) RNA molecules, each believed to code for a single polypeptide product (Gorman et al., 1981; Sanger and Mertens, 1983). The ten dsRNA species are contained in an inner core structure that contains five types of proteins, two that are major (VP3 and VP7) and three that are minor components (VP1, VP4 and VP6). The core is surrounded by an outer capsid consisting of two major proteins, VP2 and VP5, to give a complete virion particle with a diameter of approximately 69 nm.

There is a need to be able to produce antigenically active bluetongue virus proteins by recombinant DNA technology that are suitable for use as vaccines.

DESCRIPTION OF THE INVENTION

It has now been found that recombinant expression vectors can effectively be used to achieve expression of BTV structural protein VP2 and/or VP5 in antigenic form capable of raising neutralising antibodies and consequently being suitable for use as vaccine components.

Further BTV structural proteins have hitherto been expressed in insect cells, but it has not previously been demonstrated that any BTV structural proteins produced by recombinant DNA technology are capable of raising neutralising antibodies and consequently are suitable for use as vaccine components. We have now demonstrated that BTV proteins expressed in this way are suitable for use as vaccine components.

Thus according to the present invention there is provided the use as a vaccine component of a polypeptide comprising at least an antigenic portion of at least one of bluetongue virus structure proteins VP2 and VP5 in antigenic form, characterised in that said polypeptide is produced by transforming a host with a recombinant expression vector having a DNA segment coding for said polypeptide.

According to a preferred aspect of the invention, said polypeptides are produced by infecting susceptible insects or cultured insect cells with one or more expression vectors having a DNA segment coding for said polypeptides.

The invention further provides a method of obtaining a protective effect against bluetongue infection in mammals (particularly ruminants) which comprises innoculating said mammals with a polypeptide comprising at least an antigenic portion of bluetongue virus structural protein VP2 in antigenic form, characterised in that said polypeptide is produced by transforming a host with a recombinant expression vector having a DNA segment coding for said polypeptide.

As above, said polypeptide is preferably produced by infecting susceptible insects or cultured insect cells with an expression vector having a DNA segment coding for said polypeptide.

It has further been found that an enhanced protective effect may be achieved by the combined use as a vaccine component, of at least an antigenic portion of bluetongue virus structural protein VP2 (produced as described above) and a polypeptide comprising at least an antigenic portion of bluetongue virus structural protein VP5, said structural protein VP5 also being produced by transforming a host with a recombinant expression vector having a DNA segment coding for said polypeptide. As above, preferably said VP5 polypeptide is preferably produced by infecting susceptible insects or cultured insect cells with an expression vector having a DNA segment coding for said polypeptide.

Thus, preferably, said mammals are further innoculated with a second polypeptide comprising at least an antigenic portion of bluetongue virus structural protein VP5 in antigenic form, characterised in that said second polypeptide is produced by transforming a host with a recombinant expression vector having a DNA segment coding for said polypeptide. As above said host preferably comprises susceptible insects or cultured insect cells.

Also provided according to the invention is the use of a polypeptide comprising at least an antigenic portion of BTV structural protein VP2 in the manufacture of a vaccine composition for carrying out the above method, characterised in that said polypeptide is produced as described above.

The use of of a polypeptide comprising of at least an antigenic portion of BTV structural protein VP5 in the manufacture of such a vaccine composition, characterised in that said polypeptide is produced by infecting susceptible insects or cultured insect cells with an expression vector having a DNA segment coding for said polypeptide also forms part of the present invention.

According to a further aspect of the invention there is provided a vaccine composition comprising a polypeptide comprising at least an antigenic portion of bluetongue virus structural protein VP2 in antigenic form, characterised in that said polypeptide is produced as described above, preferably by infecting susceptible insects or cultured insect cells with an expression vector having a DNA segment coding for said polypeptide.

The vaccine preferably also additionally comprises a polypeptide comprising at least an antigenic portion of bluetongue virus structural protein VP5 in antigenic form, characterised in that said polypeptide is produced as described above, preferably by infecting susceptible insects or cultured insect cells with an expression vector having a DNA segment coding for said polypeptide.

Surprisingly it has been found that transformed insects and cultured insect cells are capable of producing bluetongue virus structural proteins VP2 and VP5 in morphological forms which are capable of raising neutralising antibodies in mammals.

Especially suitable expression vectors for transforming the insects or insect cells are those based on baculoviruses.

Thus for example the expression vectors used in the method of the invention may comprise a recombinant baculovirus having a DNA segment coding for a polypeptide comprising a bluetongue virus structural protein VP2 and/or VP5.

Such recombinant baculoviruses may include promoter systems native to naturally occurring baculoviruses, for example the so-called "polyhedrin" promoter, or they may include other promoter systems capable of directing expression of polypeptide in transformed insect or cultured insect cells.

Especially suitable cultured insect cells are those of *Spodoptera frugiperda*.

For the simultaneous expression of different bluetongue proteins utilizing a baculovirus-based expression system it is advantageous to use the so-called "multiple expression system" which is the subject of International Patent Application W089/01518. The procedures described in W089/01518 utilize a plasmid designated pAcVC3 which has been deposited at the National Collection of Industrial Bacteria under Accession No. NCIB12516.

pAcVC3, contains duplicated copies of the polyhedrin transcriptional machinery from *Autographa californica* nuclear polyhedrosis virus. This enables a recombinant baculovirus to be constructed which will express two foreign polypeptides simultaneously in *Spodoptera frugiperda* insect cells. In pAcVC3, a unique enzyme restriction site located downstream of each promoter allows for the insertion of two foreign genes, each of which will be placed under the control of its own copy of the polyhedrin transcriptional machinary. The promoters are present in opposite orientations to minimize the possibility of homologous sequence recombination and excision of one or other of the foreign genes.

The VP2 and/or VP5 polypeptides advantageously are produced for incorporation into vaccines according to the invention by expressing the polypeptides together with other polypeptides having the capacity to self-assemble, whereby the polypeptides are able to form assembled antigen particles, which in many instances resemble the native viruses themselves, both in morphology and antigenic properties.

The plasmid pAcVC3/10-2/10-5 has been deposited with the American Type Culture Collection located at 12301 Parklawn Drive, Rockville, Md. 20852, United States of American, on Oct. 20, 1995 in accordance with the Budapest Treaty, and has been accorded the accession number ATCC 69941.

Examples of proteins having a capacity to self-assemble are bluetongue proteins VP3 and VP7.

The production of antigen particles proteins having a capacity to self-assemble is described and claimed in our copending International Patent Application No. PCT/GB90/101049, filed Jul. 6, 1990 (corresponding to GB 8915571.7). The assembled particles so-produced can include VP2 and VP5 polypeptides.

The expression and characterisation of the BTV serotype 10 (BTV-10) VP2 and VP5 gene products using expression systems based on recombinant baculoviruses is illustrated by the following Examples. As indicated, the expressed protein has been shown to be capable of inducing a protective effect when used as a vaccine component, especially when administered in combination with the VP5 gene product.

EXAMPLE

Virus and cells

Ac NPV and recombinant baculoviruses were grown and assayed in either confluent monolayers or spinner cultures of *Spodoptera frugiperda* cells in medium containing 10% (v/v) fetal bovine serum according to the procedures described by Brown and Faulkner (1977).

DNA manipulation and construction of DNA clones

Plasmid DNA manipulations were carried out following the procedures described by Maniatis, et al., (1982). Restriction enzymes, T4 DNA ligase, mung bean nuclease and Bal 31 nuclease were purchased from Amersham International plc (Amersham, UK) and calf intestine alkaline phosphatase from Boehringer Mannheim GmbH (FGR). Two BTV-10 segment 5 DNA clones, pM113 and pJ90, representing nucleotides 1–1314 and 992–1638 of the gene respectively (Purdy et al., 1986) were used to construct a single copy of the entire gene using a unique NcoI site present in the overlapping regions and the unique EcoRV site of pBR322. Insertion of BTV-10 segment 5 and segment 2 DNA into pAcYM1

The plasmid pBR322/10-5 was digested with Pst I and the 1.6 Kb fragment containing the complete VP5 gene was recovered and digested with Bal 31 exonuclease to eliminate the terminal dC-dG sequences which were introduced during the cDNA cloning process. The product DNA was repaired with the Klenow fragment of DNA polymerase and ligated into the dephosphorylated vector pUC-4K which had previously been digested with Sal I and the overhanging 5' ends blunted by Mung bean nuclease. The recombinant pUC-4K/10-5 vectors were characterized by appropriate restriction enzyme digests and dideoxy sequence analysis of the double stranded plasmid DNA (Chen and Seeburg, 1985). One of these recombinant vectors had all of the terminal dC-dG sequences removed, this vector was digested with BamHI and the fragment containing the coding sequence of the gene isolated. This fragment was ligated into the baculovirus transfer vector pAcYM1 (Matsuura et al., 1987) which had previously been digested with BamHI and dephosphorylated. The orientation of the recombinant vectors was characterized by restriction mapping and dideoxy sequence analysis of the double stranded plasmid DNA. The baculovirus transfer vector pAcSI10.2 previously described (Inumaru and Roy, 1987) was digested with BamHI and the 2.9 Kb fragment containing the complete BTV-10 VP2 gene isolated. This fragment was ligated into the baculovirus transfer vector pAcYM1 which had previously been digested with BamHI and dephosphorylated. The orientation of the recombinant vectors was characterized by restriction mapping and dideoxy sequence analysis of the double stranded plasmid DNA.

Transfection and selection of recombinant baculoviruses

S. frugiperda cells were transfected with mixtures of infectious AcNPV DNA and pAcYM1/10-5 or pAcYM1/10-2 plasmid DNA. Recombinant baculoviruses were obtained as described previously (Inumaru and Roy, 1987). One recombinant derived from pAcYM1/10-5 was designated YM1/10-5 and one derived from pAcYM1/10-2 was designated YM1/10-2.

Extraction and characterization of viral and cellular nucleic acids

To obtain recombinant viral DNA 100 ml spinner cultures of *S. frugiperda* cells were infected at a multiplicity of 0.1 p.f.u./cell and incubated at 28° C. for 4 days. The procedures used for virus isolation and subsequent viral DNA extraction were essentially the same as those described previously (Matsuura et al., 1986). For Southern analysis (Southern, 1975) these preparations were digested to completion with BamHI and the products resolved by electrophoresis in 0.8% (w/v) agarose (BRL, Madison, Wis.) and then blotted onto Hybond-N (Amersham, UK) and dried. The blotted DNA was probed with BTV-10 segment 5 DNA or segment 2 DNA, obtained from the transfer vectors pAcYM1/10-5 or pAcYM1/10-2, that had been $^{32}P$ labelled by nick translation. The membrane was then washed and autoradiographed.

Production and immunological characterization of proteins

*S. frugiperda* cells were infected with either recombinant virus (YM1/10-5 or YM1/10-2), wild type AcNPV or mock infected at a multiplicity of 10 p.f.u./cell in 35 mm tissue culture dishes ($1.5\times10^6$ cells/dish) and incubated at 28° C. for 24 hours. For analysis of protein by immunoblotting or coomassie blue staining of SDS-PAGE gels the cells were harvested and washed twice in cold phosphate buffered saline (PBS) and then resuspended in 100 $\mu$l of RIPA buffer (0.05M Tris-Cl, 0.15M NaCl, 1% (v/v) TRITON X-100, 1% (w/v) sodium deoxycholate, 0.01M EDTA, pH 7.4). For analysis of proteins by immunoprecipitation the cells were subsequently incubated at 28° C. for 1 hour in methionine and serum free medium to reduce the intracellular methionine pool. The cells were then labelled with 30 $\mu$Ci of [$^{35}$S]-methionine (Amersham, 800 Ci/mmol) in methionine and serum free medium for 1 hour at 28° C. and then chased for varying times at 28° C. with medium containing unlabelled methionine. At the end of the chase period the cells were washed twice in cold PBS and resuspended in 100 $\mu$l of RIPA buffer. Fifty $\mu$l aliquots of these extracts were then incubated with 50 $\mu$l of a 1 in 50 dilution of rabbit BTV-10 antisera at 37° C. for 90 minutes. Then 25 $\mu$l of a 100 mg/ml suspension of protein A-sepharose CL-4B beads were added and the mixture incubated at 37° C. for a further two hours. At the end of this time the beads were washed twice with ice cold RIPA buffer and once with ice cold PBS and the immune complexes were removed from the beads by boiling for 5 minutes in SDS-PAGE sample buffer (2.3% (w/v) SDS, 10% (v/v) glycerol, 5% (v/v) mercaptoethanol, 62.5 mM Tris-Cl, 0.01% (w/v) bromophenol blue, pH 6.8). Aliquots of the supernatant were subjected to electrophoresis in 5% to 15% gradient gels of acrylamide as described by Laemmli (1970). After electrophoresis the gels were fixed in 40% (v/v) methanol, 10% (v/v) acetic acid in water, dried and exposed to X-ray film.

Production of antisera in mice and rabbits

Recombinant VP5 and VP2 were run on 10% SDS-PAGE gels and the protein bands visualized by staining in 0.25M KCl and destaining in tap water, both at 4° C. The bands corresponding to the recombinant proteins were excised and macerated by passing the gel through a 23 G syringe needle before use for immunization. In the case of rabbits each animal received one intra-muscular injection of antigen in Freunds complete adjuvant followed by three injections of antigen in Freunds incomplete adjuvant on days 11, 20 and 52. The animal was terminally bled by cardiac puncture 29 days after the last injection. For mice each animal recieved one injection of antigen in Freunds complete adjuvant intra-peritoneally followed by two injections of antigen in Freunds incomplete adjuvant on day 7 and day 19, then $5\times10^6$ Ehrlich's ascites cells on day 25 and a final injection of antigen in Freunds incomplete adjuvant on day 26. Ascitic fluids were removed at intervals from day 28 to day 33. For mouse antisera raised to whole cells, *S. frugiperda* cells infected with YM1/10-5, YM1/10-2 or AcNPV were harvested 2 days post infection, washed twice in PBS and injected into mice. Each animal received $3\times10^6$ cells intraperitoneally on days 0 and 21 and the animals were terminally bled on day 42.

Immunoblotting

SDS-PAGE separated samples were subjected to electrophoretic transfer, for 3 hours at 0.8mA/cm$^2$, onto DURAPORE membrane (Millipore Corp.) using a semi-dry electroblotter (Sartoblot II, Sartorius Corp.). The blotted membrane was soaked overnight at 4° C. in blocking buffer (5% (w/v) skimmed milk, 0.5% (v/v) TWEEN-20 in PBS). The membrane was then treated for 90 minutes with the appropriate antisera diluted in blocking buffer and then washed with PBST (0.5% (v/v) Tween-20 in PBS). This was followed by treatment for 90 minutes with the appropriate anti IgG antiserum coupled to alkaline phosphatase (Sigma Chemical Co.) before a final wash in PBST. Bound antibodies were detected using FAST BB SALT and β-napthyl phosphate (Sigma Chemical Co.) as a substrate.

Plaque reduction neutralization tests

Antisera and BTV dilutions were done in PBS. 100 $\mu$l aliquots of diluted antisera were mixed with 100 $\mu$l aliquots of diluted virus in 24-well tissue culture plates (Sterilin, Feltham, England) and incubated at 4° C. overnight. As controls normal sera or PBS alone were used. Then 0.5 ml of a suspension of Vero cells ($2\times10^5$ cells/ml in L15 medium supplemented with 2% (v/v) fetal calf serum) was added to each well and the plates were incubated at 35° C. for 4 hours. The cells were then overlaid with 0.75% (w/v) carboxymethyl cellulose in L15 medium. After incubation for four days at 35° C. the cells were fixed with 10% (v/v) formalin in PBS for 15 minutes and stained with 1.5% (w/v) crystal violet in 95% (v/v) ethanol for 15 minutes. Plaques in each well were then counted.

Construction of recombinant viruses (YM1/10-5, YM1/10-2)

Baculovirus transfer vector pAcYM1/10-5 containing the entire sequence representing the BTV-10 M5 RNA segment was constructed according to the scheme in FIG. 1. The insert was complete at the 5' end, with an additional G nucleotide derived from pUC-4K, and the 3' end had 24 nucleotides missing (FIG. 2). Thus the transfer vector pAcYM1/10-5 contained the entire open reading frame coding for VP5 downstream of the AcNPV polyhedrin promotor. The orientation of the L2 DNA insert in relation to the polyhedrin promotor of pAcYM110-2 was determined by DNA sequence analysis (FIG. 2). In order to transfer the VP5 and the VP2 genes into the AcNPV genome *S. frugiperda* cells were cotransfected with infectious AcNPV DNA and either pAcYM1/10-5 or pAcYM1/10-2 transfer vector DNA. Polyhedrin negative, recombinant progeny viruses were selected and after three plaque purifications high titer stocks ($10^8$ p.f.u./ml) of two recombinant viruses, YM1/10-5 and YM1/10-2, were prepared on monolayers of *S. frugiperda* cells.

Analysis of recombinant viral DNA

In order to confirm the presence of the DNA coding for VP5 and VP2 in the recombinant baculoviruses, DNA from YM1/10-5, YM1/10-2 and wild type AcNPV was isolated and subjected to Southern blot analysis. As shown in FIG. 3, both YM1/10-5 recombinant viral DNA and pAcYM/1/10-5 transfer vector DNA, when digested with BamHI, both contained only one band of equal size that hybridized to the nick-translated segment 5 DNA probe. No bands were detected, under the same conditions, in the AcNPV viral DNA digested with BamHI. Southern analysis of BamHI digested YM1/10-2 viral DNA with nick-translated segment 2 DNA also confirmed the presence of segment 2 DNA in the YM1/10-2 recombinant baculovirus.

Expression of VP5 and VP2 in *S. frugiperda* cells

Infection of *S. frugiperda* cells with YM1/10-5 or YM1/10-2 did not produce visible nuclear inclusions. When extracts of these cells were run on a 10% SDS-PAGE gel and stained with Coomassie blue in each case an extra band was observed that was not present in mock or AcNPV infected cells (FIG. 4). In the case of YM1/10-5 the extra band corresponded to the expressed VP5 size of 59 Kd. For YM1/10-2 the expressed VP2 105 Kd was observed. Neither YM1/10-5 or YM1/10-2 infected cells produced the 29 Kd polyhedrin (Pol) band seen in AcNPV infected cells. Immunoblotting with rabbit antisera raised to BTV-10 showed that both the expressed recombinant VP5 and VP2 proteins were recognised and co-migrated with the authentic proteins in BTV-10 infected BHK cells (FIG. 5). In the case of the expressed VP2 the antisera recognized one major band of 105 Kd whilst in the case of the expressed VP5 the antisera recognized one band of 59 Kd and and a number of other bands of lower molecular weight. The antisera did not recognize any proteins in AcNPV infected S. frugiperda cells.

Both rabbit antisera raised to the expressed VP2 and mouse ascitic fluid raised to the expressed VP5 recognized the corresponding authentic proteins in BTV-10 infected BHK cells (FIG. 5), neither the preimmune rabbit sera or the control ascitic fluid recognised these proteins. To determine if the bands of less than 59 Kd seen on immunoblotting the expressed VP5 protein represented proteolytic degradation products or premature terminations of mRNA translation an immune precipitation of $^{35}$S-methionine pulse-chase labelled YM1/10-5 infected S. frugiperda cells was undertaken. As shown in FIG. 6, rabbit antiserum raised to BTV-10 precipitated a band of 59 Kd from YM1/10-5, but not from mock or AcNPV, infected cells at all of the time points. A series of bands of molecular weights less than 59 Kd were also precipitated from only the YM1/10-5 infected cells. The intensity of these smaller bands increased up to 8 hours post-labelling and then decreased. The precipitation of a 29 Kd protein from AcNPV infected cells was probably due to the non-specific precipitation of polyhedral inclusion bodies (data not shown).

Neutralization of BTV by antisera raised to recombinant VP5 and VP2

Antisera were raised to recombinant VP5 and VP2 proteins purified by SDS-PAGE in mice and rabbits respectively. Antisera to whole S. frugiperda cells infected with YM1/10-5, YM1/10-2 or AcNPV were also raised in mice. All of these sera, along with preimmune rabbit sera and control ascitic fluid, were tested for their ability to neutralize BTV in vitro by plaque reduction neutralization tests (Table 1). Rabbit antisera raised to VP2 had a neutralizing titer of greater than 1:640 against BTV-10 and greater than 1:160 against BTV-11 and BTV-17. The sera had no neutralizing activity against BTV-13. Mouse ascitic fluid raised to the expressed VP5 had no neutralizing antibody titer to BTV-10, 11, 13 or 17. In the case of mouse antisera raised to whole S. frugiperda cells infected with either YM1/10-2, YM1/10-5 or AcNPV four mice were immunized, and tested for each condition. The mean neutralization titers for YM1/10-2 and YM1/10-5 infected cells was 1:205 and 1:51 respectively. The mean titer for AcNPV infected cells was 1:55 and the neutralization titer induced by YM1/10-2 infected cells was significantly greater than this, as judged by the two sample t-test, whilst the neutralization titer of the sera raised to YM1/10-5 infected cells was not.

TABLE 1

Plaque reduction neutralization titers of antisera raised to expressed VP2 and VP5

| | BTV Serotypes | | | |
|---|---|---|---|---|
| Antisera | 10 | 11 | 13 | 17 |
| Rabbit VP2 Antisera | >640 | >160 | 0 | >160 |
| Preimmune rabbit sera | 0 | 0 | 0 | 0 |
| Mouse VP5 ascitic fluid | 0 | 0 | 0 | 0 |
| Control ascitic fluid | 0 | 0 | 0 | 0 |
| Mouse antisera to: | | | | |
| YM1/10-2 infected S. frugiperda cells | 205 ± 74* (n = 4) | — | — | — |
| YM1/10-5 infected S. frugiperda cells | 51 + 23+ (n = 4) | — | — | — |
| AcNPV infected S. frugiperda cells | 55 + 40 (n = 4) | — | — | — |

*Significantly different from AcNPV infected S. frugiperda cells at the P = 0.05 level.
+Not significantly different from AcNPV infected S. frugiperda cells at the P = 0.05 level.

Recombinant baculoviruses have been constructed that contain DNA sequences coding for the BTV-10 proteins VP5 and VP2 downstream of the polyhedrin promotor. When S. frugiperda cells are infected with these recombinants VP5 and VP2 proteins are synthesized to a high level in place of the polyhedrin protein. The expression of VP5 is not to as high a level as that of VP2 as judged by Coomassie blue staining of SDS-PAGE gels. This would appear to be at least partially due to proteolytic degradation since immunoblotting of the expressed proteins revealed a series of immunologically related species, of lower molecular weights, in the case of VP5 but not for VP2. That these species represent post-translational proteolytic degradation rather than premature terminations of translation is supported by the observation that immune precipitation of $^{35}$S-methionine pulse labelled YM1/10-5 infected S. frugiperda cell extracts showed that the degraded species increased in amount with the post-labelling chase period. Both the expressed VP5 and VP2 were recognized by antiserum raised to BTV-10 virus and antisera raised to these expressed proteins recognized authentic BTV-10 VP2 and VP5. Thus it would appear that the baculovirus expressed proteins have immunological properties closely related to the authentic BTV-10 proteins. This is corroborated by the fact that the expressed VP2 could induce neutralizing antibodies.

The use of an improved baculovirus transfer vector pAcYM1 (Matsuura et al., 1987) gave higher levels of expression of VP2 in baculovirus, and induced higher titers of neutralizing antibodies than previously reported for the transfer vector pAcRP6S (Inumaru and Roy, 1987). Expressed VP2 also induced neutralizing antibodies to BTV-11 and BTV-17 but not BTV-13, albeit at a lower titer than to BTV-10, and this pattern of cross-serotype neutralization reflects the pattern of homologies between the VP2 proteins of the various serotypes (Yamaguchi et al., 1988). The use of SDS-PAGE purified expressed VP2 as an antigen was successful in inducing neutralizing antibodies which was not the case for VP2 isolated in the same manner from BTV virions. In contrast to these data the expressed VP5 protein purified by SDS-PAGE did not induce neutralizing antibodies against BTV-10. Immunization of mice with whole S. frugiperda cells infected with YM1/10-5 recombinant also failed to induce neturalizing antibodies but immunization with cells infected with the YM1/10-2 recombinant did induce neutralizing antibodies. Therefore the purification of the expressed proteins by SDS-PAGE did not appear to interfere with their ability to induce neutralizing antibodies. The data presented indicates that the outer capsid protein VP2 plays a direct role in neuralization of BTV whilst VP5 does not.

Vaccine Assessments

Experiments were carried out to assess the effectiveness of various recombinant polypeptides and combinations as vaccines for eliciting a protective effect in sheep against BTV-10. Comparisons were made between antigens extracted from native virus and recombinant polypeptide. The results are given in Table 2.

From the results it can be seen that soluble VP2 from purified BTV virus appeared to be negative whereas all sheep that had received polypeptide produced in insect cells by recombinant baculovirus were solidly protected.

Particularly high level of protection were observed in sheep that had received a combination of recombinant VP2 and VP5.

AcNPV DNA. Progeny viruses were titrated using confluent monolayers of S. frugiperda cells and putative recombinants were selected on the basis of their polyhedrin-negative phenotype (ca 0.1% frequency). After successive rounds of plaque purification, a high titre viral stock was prepared.

S. frugiperda cells infected with the recombinant baculovirus synthesized two unique protein species in plate of the 29KDa polyhedrin protein seen in wild-type AcNPV infected cells (FIG. 8A).

The sizes of the expressed proteins agree with those expected or VP2 and VP5 calculated from their amino acid compositions (i.e., 111,112 Da and 59,136 Da respectively).

Since the levels of expression were below that which could be determined by staining, confirmation that the expressed proteins represented authentic BTV proteins was provided by Western blot analyses using antisera raised to BTV-10 virus particles (FIG. 8B).

B. VP3/VP7 Construct

The construction of recombinant expression vector pAcVC3.BTV-10.7.BTV-17.3 is illustrated in FIG. 9.

| ANTIGEN | ADJU-VANT | INOCULATIONS (DATE) | | | *SERUM NEUTRALIZATION TITERS AGAINST BTV-10 (DATE) | | | | | | | | CLINICAL REACTION INDEX (CRI) |
|---|---|---|---|---|---|---|---|---|---|---|---|---|---|
| | | 14/12 88 | 4/1 | 25/1 | 18/1 | 25/1 | 31/1 | 3/2 | 6/2 | 13/2 | 20/2 | 27/2 | |
| BTV-10VP2 | − | ✓ | ✓ | ✓ | 32 | 32 | 64 | 64 | 32 | 64 | 16 | 8 | ? |
| 250–500 µg | | ✓ | ✓ | ✓ | 32 | 32 | 32 | 32 | 16 | 8 | 8 | 4 | 1.4 |
| | ∓ | ✓ | ✓ | ✓ | 16 | 16 | 32 | 32 | 32 | 16 | 12 | 8 | 0.0 |
| | + | ✓ | ✓ | ✓ | <4 | 4 | 16 | 16 | 16 | 8 | 8 | 8 | 3.1 |
| BTV-10/11/17 | − | ✓ | ✓ | ✓ | <4 | 4 | 16 | 16 | 16 | 8 | 8 | 8 | 0.0 |
| VP2 | | ✓ | ✓ | ✓ | 16 | 16 | 64 | 64 | 32 | 32 | 16 | 12 | 0.0 |
| | ∓ | ✓ | ✓ | ✓ | 16 | 16 | 32 | 32 | 32 | 16 | 12 | 8 | 0.0 |
| | + | ✓ | ✓ | ✓ | 8 | 16 | 32 | 32 | 32 | ? | 16 | 12 | 0.0 |
| BTV-10VP2 | − | ✓ | ✓ | ✓ | <4 | <4 | 16 | 8 | 8 | 8 | 4 | 4 | 0.0 |
| & VP5 | | ✓ | ✓ | ✓ | <4 | 4 | 16 | 8 | 8 | 8 | ? | 4 | 0.0 |
| | ∓ | ✓ | ✓ | ✓ | >32 | 128 | 512 | 256 | 128 | 128 | 128 | 96 | 0.0 |
| | + | ✓ | ✓ | ✓ | 32 | 64 | 128 | 128 | 64 | 32 | 32 | 24 | 0.0 |
| BTV-10VP1, | − | ✓ | ✓ | ✓ | 8 | <4 | 8 | 8 | 8 | 16 | 16 | 16 | 0.0 |
| VP2, VP3, VP5, | | ✓ | ✓ | ✓ | 16 | 4 | 8 | 8 | 8 | 24 | 24 | 12 | 0.0 |
| VP6, VP7, NS1, | ∓ | ✓ | ✓ | ✓ | >32 | 128 | 256 | 256 | 128 | 64 | 64 | 16 | 0.0 |
| NS2, NS3 | + | ✓ | ✓ | ✓ | >32 | 64 | 128 | 128 | 64 | 64 | 48 | 24 | 0.0 |
| BTV-10VP2 | − | ✓ | ✓ | 0 | >32 | 64 | 16 | 16 | 16 | 16 | ? | 8 | 0.0 |
| 500–1000 µg | | ✓ | ✓ | 0 | >32 | 64 | 32 | 32 | 16 | 16 | 12 | 8 | 0.0 |
| | ∓ | ✓ | ✓ | 0 | 32 | 32 | 16 | 16 | 16 | 8 | 6 | 4 | 0.0 |
| | + | ✓ | ✓ | 0 | 16 | 8 | <4 | <4 | <4 | ? | >4 | >4 | 0.0 |
| BTV-10VP2 | − | ✓ | ✓ | 0 | >32 | 128 | 32 | 32 | 32 | 16 | 16 | 8 | 0.0 |
| 1000–2000 µg | | ✓ | ✓ | 0 | >32 | 64 | 16 | 16 | 16 | 16 | 8 | 8 | 0.0 |
| | ∓ | ✓ | ✓ | 0 | >32 | 128 | 64 | 64 | 32 | 32 | 32 | 16 | 0.0 |
| | + | ✓ | ✓ | 0 | >32 | 512 | 128 | 128 | 128 | 64 | 64 | 32 | 0.0 |
| Solubilized | + | ✓ | ✓ | ✓ | <4 | <4 | <4 | <4 | >4 | >4 | <4 | <4 | 4.6 |
| BTV-10VP2 | + | ✓ | ✓ | ✓ | <4 | <4 | <4 | <4 | <4 | >4 | <4 | <4 | 5.1 |
| Saline | − | ✓ | ✓ | ✓ | <4 | <4 | <4 | <4 | <4 | <4 | <4 | <4 | 6.0 |
| | | ✓ | ✓ | ✓ | <4 | <4 | <4 | <4 | <4 | <4 | <4 | <4 | 7.4 |
| | ∓ | ✓ | ✓ | ✓ | <4 | <4 | <4 | <4 | <4 | <4 | <4 | <4 | 3.7 |
| | + | ✓ | ✓ | ✓ | <4 | <4 | <4 | <4 | <4 | <4 | <4 | <4 | 5.0 |

*Reciprocal of the dilution that caused a 50% plaque reduction

EXAMPLE 2

This example describes the production of antigenically active particles comprising bluetongue proteins Bt VP2, VP3, VP5 and VP7.

A. VP2/VP5 Construct

A VP2-VP5 recombinant plasmid was constucted by the manipulations shown in FIG. 7. They involved excision of the L2 and M5 genes from their PAcYMI single expression transfer vectors and insertion into the BamHI and BgIII sites (respectively) of the multiple expression vector pAcVC3. Recombinant baculoviruses were prepared by the established procedure of co-transfecting S. frugiperda insect cells with the recombinant plasmid DNA and infectious wild-type The initial step for the expression of the BTV genes was to synthesize cDNA copies of the double stranded RNA L3 and M7 segments. Although these were isolated from different serotypes (17 and 10 respectively), the L3 gene is very highly conserved with an amino acid homology of greater than 99%.

Homopolymeric tails introduced to aid the cloning procedure were removed by limited Bal31 exonuclease digestion before insertion of the genes into the pAcVc3 transfer vector. Recombinant baculoviruses were prepared by the established procedure of co-transfecting S. frugiperda cells with the dual expression plasmid DNA and wild-type AcNPV DNA.

Progeny viruses were titrated using confluent monolayers of S. frugiperda cells and putative recombinants selected on the basis of their polyhedrin negative phenotype (ca 0.1% fequency). After successive rounds of plaque purification of high titre viral stock was prepared. S. frugiperda cells infected with the recombinant baculovirus synthesized two unique proteins species in place of the 29kDa polyhedrin protein seen in wild-type AcNPV infected cells (FIG. 10A).

The sizes of the expression proteins agree with those expected for VP3 and VP7 calculated from their amino acid compositions (103,226 KDa and 385,48 KDa respectively). Confirmation that these expressed proteins represented authentic BTV proteins was provided by Western blot analysis with antisera raised to BTV-10 virus particles (FIG. 10B).

C. Dual Expression of VP2/VP5 and VP3/7 Constructs

To assess the interaction of these proteins with the BTV core-like particles, insect cells were co-infected with both dual recombinant baculoviruses (in order to co-express VP2, VP3, VP5 and VP7).

The cells were harvested at 48 hours post-infection, lysed with the non-ionic detergent Nonidet P40, and particles purified to homogeneity by centrifugation on discontinuous sucrose gradients. When examined under the electron microscope, empty double-shelled particles were observed consisting of a core surround by a thick outer capsid (FIG. 11A, large arrow). The diameters of the largest particles were estimated to be of the order of 85 nm, i.e., comparable to those of BTV (FIG. 11B). Some simple core-like particles were also observed in the preparation (FIG. 11A, thin arrows). Their diameters were estimated to be of the order of 65 nm. A range of intermediate structures were also observed, apparently with varying amounts of the outer capsid proteins attached.

These may reflect different stages in particle assembly. Interestingly, the centre areas of both types of particles (cores, and virus-like particles) exhibited an icosahedral configuration. The smaller size of the central area of the virus-like particles is presumably due to the presence and density of the outer capsid proteins. The icosahedral configuration of the centre was also apparent in several authentic BTV particles where stain had penetrated the particles. The purified expressed particles were analysed by SDS-PAGE and Western Immunoblot and shown to contain large amounts of VP2 and VP5 (FIG. 8), in addition to VP3 and VP7.

The autheniticity of the expressed empty double-shelled virus particles was assessed by their immunogenicity and haemagglutinating acitvity. Guinea pig sera raised against purified core-like particles and double-shelled virus-like particles were tested for their neutralizing activity against BTV-10. As expected, sera raised to the cores exhibited no neutralizing activity while in a 50% plaque reduction test substantial neutralization was demonstrated by the sera raised to the double-shelled particles at a dilution of 1:10, 000. Monospecific sera raised to VP2 gave titres of <500. Purified double-shelled particles also exhibited haemagglutinating titers (Table 3), comparable to those observed with authentic virus. Purified cores did not haemagglutinate. VP2 has been demonstrated to be the haemagglutinating protein in authentic bluetongue virus.

These data are supported by the inhibitory effect of monospecific sera raised to VP2 on the haemagglutination activity of the double-shelled particles. Monspecific sera raised to the other component proteins (VP3, VP5 and VP7) had essentially no effect (Table 3). Unlike authentic BTV, the virus-like particles were non-infectious when assayed in mammalian cells.

Several interesting conclusions regarding BTV morphogenesis can be drawn from the results described. The outer capsid proteins VP2 and VP5 do not attach individually to the core-like particles. This suggests that these proteins may interact before attaching to the core, or alternatively they may bind sequentially until a complete particle is produced. As with the formation of core-like particles in insect cells, the addition of the outer-capsid is not dependent on the presence of the BTV non-structural proteins (NS1, NS2, NS3), or viral double-standard RNA. or the minor proteins VP1, VP4, VP6.

TABLE 3

Haemagglutination analysis of BTV double-shelled virus-like particles

| Substrate | Haemagglutination titer |
|---|---|
| Single-shelled core-like particles | <2 |
| Double-shelled virus-like particles | 2048 |

| Sera tested | Haemagglutination-Inhibition titer |
|---|---|
| Preimmune rabbit | 16 |
| Rabit anti VP2 | >1024 |
| Rabbit anti VP7 | 2 |
| Preimmune mouse | 4 |
| Mouse anti VP5 | 8 |
| Mouse anti VP3 | 32 |

S. frugiperda cells infected with the appropriate recombinant baculoviruses were lysed with Nonidet P-40 and double-shelled virus-like particles, or core-like particles, were isolated on discontinuous sucrose gradients. The haemagglutination titer of this material was assayed at 4° C. using 0.25% rabbit erythrocytes as the indicator. Titers are expressed as the reciprocal of the highest serial dilution that gave complete haemagglutination. Antisera raised to baculovirus expressed BTV proteins were used in haemagglutination-inhibition tests. The inhibition titers are expressed as the reciprocal of the highest serial dilution of sera that gave complete inhibition of haemagglutination.

D. Vaccine Assessments

Additional experiments were carried out to assess the effectiveness of various recombinant polypeptides and combinations as vaccines for eliciting a protective effect in sheep against BTV-10.

The results are given in Tables 4 and 5.

TABLE 4

Serum plaque reduction titers of sheep inoculated with recombinant BTV antigens

| GROUP NO. | ANTIGENS | SHEEP NO. | ADJU-VANT | INOCULATION (Day) | | | *SERUM NEUTRALIZATION TITERS AGAINST BTV-10 (Days) | | | | | | | |
|---|---|---|---|---|---|---|---|---|---|---|---|---|---|---|
| | | | | 0 | 21 | 42 | 25 | 42 | 48 | 50 | 52 | 60 | 67 | 74 |
| I | VP2: ~50 µg | 1 | − | ✓ | ✓ | ✓ | 32 | 32 | 64 | 64 | 32 | 64 | 16 | 8 |
| | | 2 | − | ✓ | ✓ | ✓ | 32 | 32 | 32 | 32 | 16 | 8 | 8 | 4 |
| | | 3 | + | ✓ | ✓ | ✓ | 16 | 16 | 32 | 32 | 32 | 16 | 12 | 8 |
| | | 4 | + | ✓ | ✓ | ✓ | <4 | 4 | 16 | 16 | 16 | 8 | 8 | 8 |
| II | VP2: ~100 µg | 5 | − | ✓ | ✓ | − | >32 | 64 | 16 | 16 | 16 | 16 | 8 | 8 |
| | | 6 | − | ✓ | ✓ | − | >32 | 64 | 32 | 32 | 16 | 16 | 12 | 8 |
| | | 7 | + | ✓ | ✓ | − | 32 | 32 | 16 | 16 | 16 | 8 | 6 | 4 |
| | | 8 | + | ✓ | ✓ | − | 16 | 8 | <4 | <4 | <4 | <4 | <4 | <4 |
| III | VP2: ~200 µg | 9 | − | ✓ | ✓ | − | >32 | 128 | 32 | 32 | 32 | 16 | 16 | 8 |
| | | 10 | − | ✓ | ✓ | − | >32 | 64 | 16 | 16 | 16 | 16 | 8 | 8 |
| | | 11 | + | ✓ | ✓ | − | >32 | 128 | 64 | 64 | 32 | 32 | 32 | 16 |
| | | 12 | + | ✓ | ✓ | − | >32 | 512 | 128 | 128 | 128 | 64 | 64 | 32 |
| IV | VP2: ~50 µg VP5: ~20 µg | 13 | − | ✓ | ✓ | ✓ | <4 | <4 | 16 | 8 | 8 | 8 | 4 | 4 |
| | | 14 | − | ✓ | ✓ | ✓ | <4 | 4 | 16 | 8 | 8 | 8 | 4 | 4 |
| | | 15 | + | ✓ | ✓ | ✓ | >32 | 128 | 512 | 256 | 128 | 128 | 128 | 96 |
| | | 16 | + | ✓ | ✓ | ✓ | 32 | 64 | 128 | 128 | 64 | 32 | 32 | 24 |
| V | VP1, VP5: (~20 µg, each) VP2; VP3: (~50 µg, each) VP6, VP7: (~100 µg, each) NS1; NS2: (~200 µg, each) NS3: (~20 µg) | 17 | − | ✓ | ✓ | − | 8 | >4 | 8 | 8 | 8 | 16 | 16 | 16 |
| | | 18 | − | ✓ | ✓ | − | 16 | 4 | 8 | 8 | 8 | 24 | 24 | 12 |
| | | 19 | + | ✓ | ✓ | − | >32 | 128 | 256 | 256 | 128 | 64 | 64 | 16 |
| | | 20 | + | ✓ | ✓ | − | >32 | 64 | 128 | 128 | 64 | 64 | 48 | 24 |
| VI | SALINE | 21 | − | ✓ | ✓ | ✓ | <4 | <4 | <4 | <4 | <4 | <4 | <4 | <4 |
| | | 22 | − | ✓ | ✓ | ✓ | <4 | <4 | <4 | <4 | <4 | <4 | <4 | <4 |
| | | 23 | + | ✓ | ✓ | ✓ | <4 | <4 | <4 | <4 | <4 | <4 | <4 | <4 |
| | | 24 | + | ✓ | ✓ | ✓ | <4 | <4 | <4 | <4 | <4 | <4 | <4 | <4 |

*Reciprocal of the dilution that caused a 50% plaque reduction
Pairs of animals were inoculated with (+) or without (−) Incomplete Freund's adjuvant on the days indicated (✓)

TABLE 5

Immune status of vaccinated sheep after virulent virus challenge

| GROUP NO. | INOCULUM | SHEEP NO. | SERUM NEUTRALIZATION TITERS AGAINST BTV-10 (21 DAYS POST CHALLENGE) | CLINICAL REACTION INDEX | VIREMIA* (DAYS POST-CHALLENGE) |
|---|---|---|---|---|---|
| I | VP2: ~50 µg | 1 | 160 | 0.0 | − |
| | | 2 | 640 | 1.4 | 4–6 |
| | | 3 | 40 | 0.0 | − |
| | | 4 | 320 | 3.1 | − |
| II | VP2: ~100 µg | 5 | 40 | 0.0 | − |
| | | 6 | <20 | 0.0 | − |
| | | 7 | <20 | 0.0 | − |
| | | 8 | 80 | 0.0 | − |
| III | VP2: ~200 µg | 9 | 80 | 0.0 | − |
| | | 10 | 40 | 0.0 | − |
| | | 11 | 80 | 0.0 | − |
| | | 12 | <20 | 0.0 | − |
| IV | VP2: ~50 µg VP5: ~20 µg | 13 | 40 | 0.0 | − |
| | | 14 | 40 | 0.0 | − |
| | | 15 | 120 | 0.0 | − |
| | | 16 | 60 | 0.0 | − |
| V | VP1, VP5:(~20 µg, each) VP2; VP3: (~50 µg, each) VP6; VP7: (~100 µg, each) NS1; NS2: (~200 µg,each) NS3: (~20 µg) | 17 | 20 | 0.0 | − |
| | | 18 | 20 | 0.0 | − |
| | | 19 | <20 | 0.0 | − |
| | | 20 | 20 | 0.0 | − |
| VI | SALINE | 21 | >640 | 7.4 | 4–9 |
| | | 22 | 640 | 5.0 | 4–10 |
| | | 23 | 640 | 4.6 | 4–9 |
| | | 24 | >640 | 5.1 | 4–10 |

*Viremia assayed in eggs; − indicates none detected, numbers refer to days sheep blood tested positive for viremia.
Clinical Reaction index: (a + b + c): (a) the fever score - the cumulative total of fever readings above 40° on days 3–14 after challenge (maximum score 12); (b) the lesion score - lesions of the mouth, nose and feet were each scored on a scale of 0–4 and added together (maximum score 12); (c) the death score - 4 points if death occurred within 14 days post-challenge.

BRIEF DESCRIPTION OF THE DRAWINGS

The invention is described with reference to the accompanying drawings, in which FIG. 1 Schematic diagrams of the construction of the transfer vector pAcYM1/10-5 as described in Methods.

FIG. 2 Sequence around the insertion sites of transfer vectors pAcYM1/10-5 and pAcYM1/10-2. BTV coding sequences are underlined and start and stop codons are boxed.

Figure 9A:
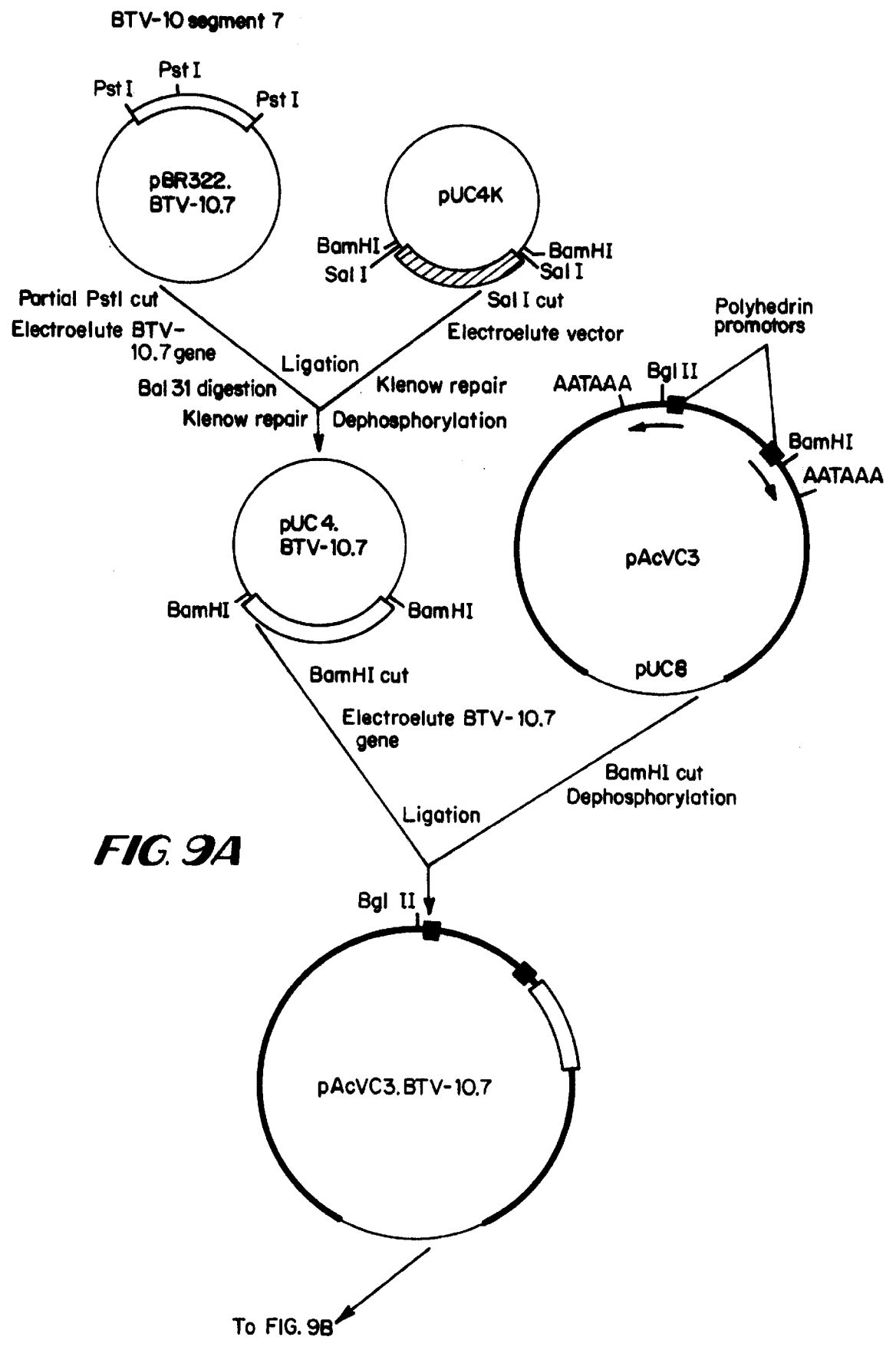
Figure 9B:
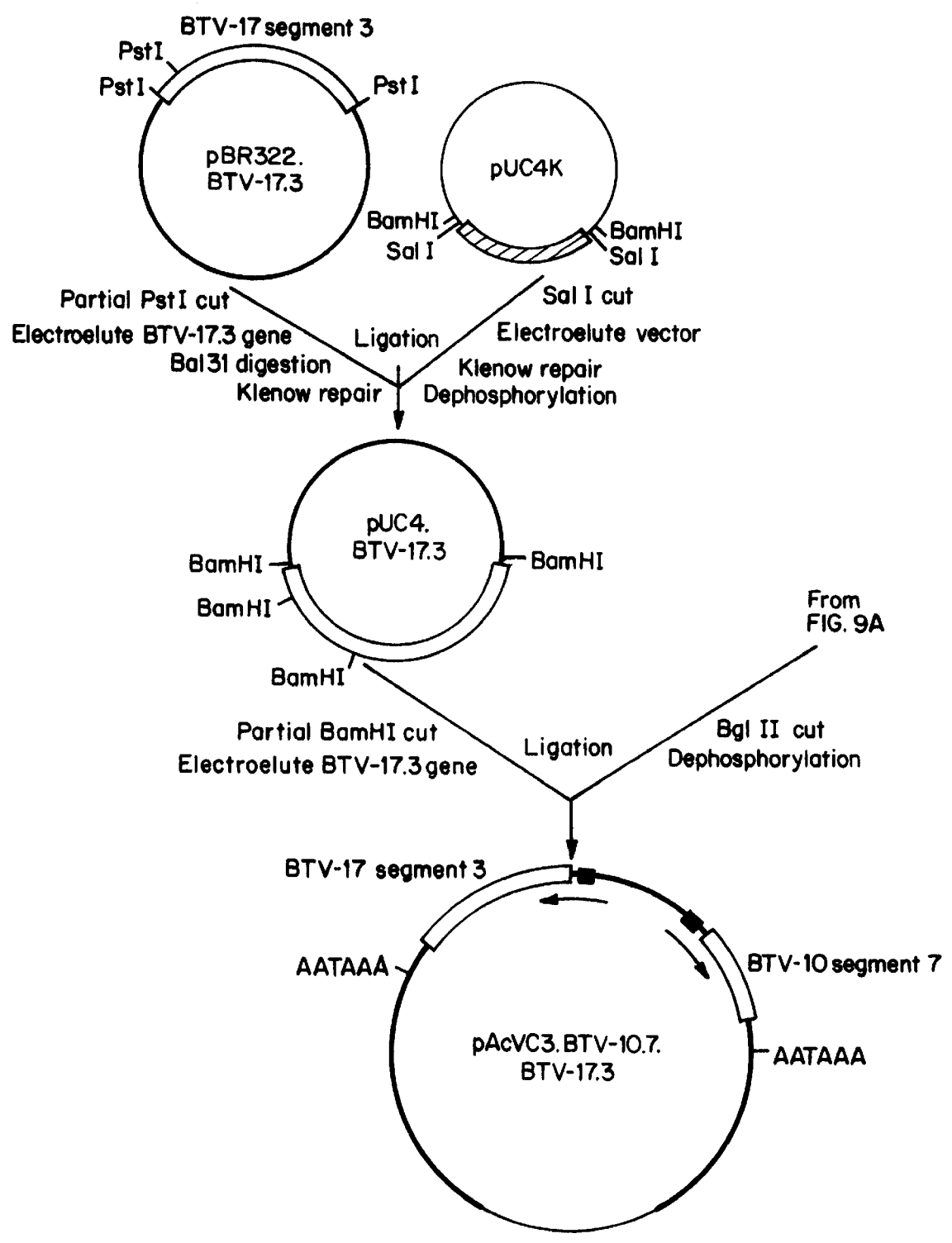

FIGS. 9A and 9B. Construction diagram of the dual expression transfer vector showing the appropriate manipulations for the insertion of the BTV L3 and M7 genes.

FIGS. 11A, 11B and 11C. Electron micrographs of empty BTV core particles synthesized in insect cells by a recombinant baculovirus expressing both major BTV core proteins VP3 and VP7 (A) sections of S. frugiperda cells infected with the recombinant (1), or wild-type AcNPV virus (2). (B) purified expressed particles (3) compared with authentic BTV core particles (4).

Figure 1:
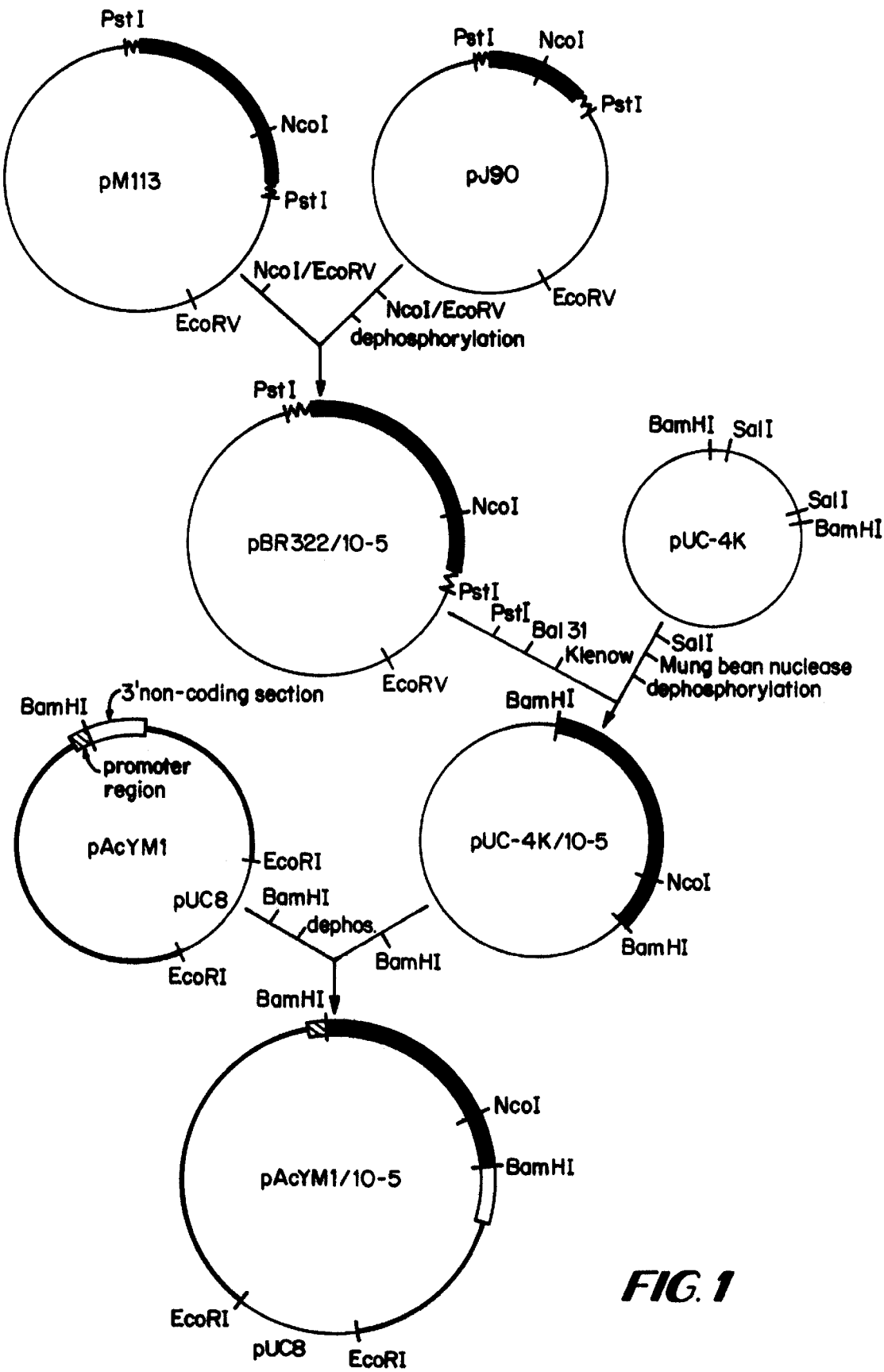
Figure 3:
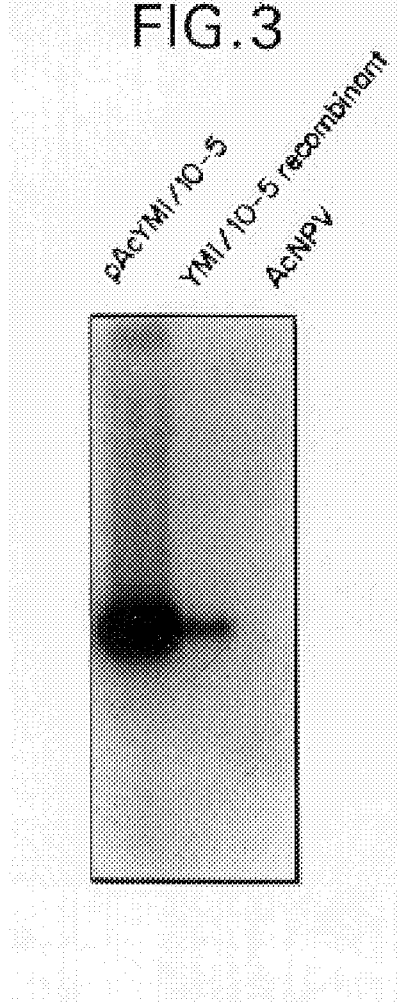
FIG. 3 Southern analysis of viral DNA isolated from YM1/10-5 and AcNPV infected S. frugiperda cells and pAcYM1/10-5 transfer vector DNA probed with nick translated segment 5 DNA as described in Methods.
Figure 4:
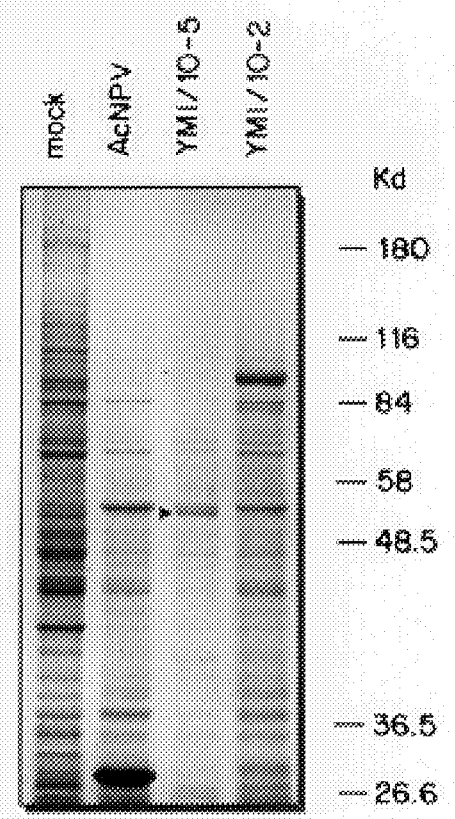
FIG. 4 SDS-PAGE analysis of mock, AcNPV, YM1/10-5 and YM1/10-2 infected S. frugiperda cells. The positions of the VP5, VP2 and polyhedrin protein bands are marked along with the positions of molecular weight markers run at the same time.
Figure 5:
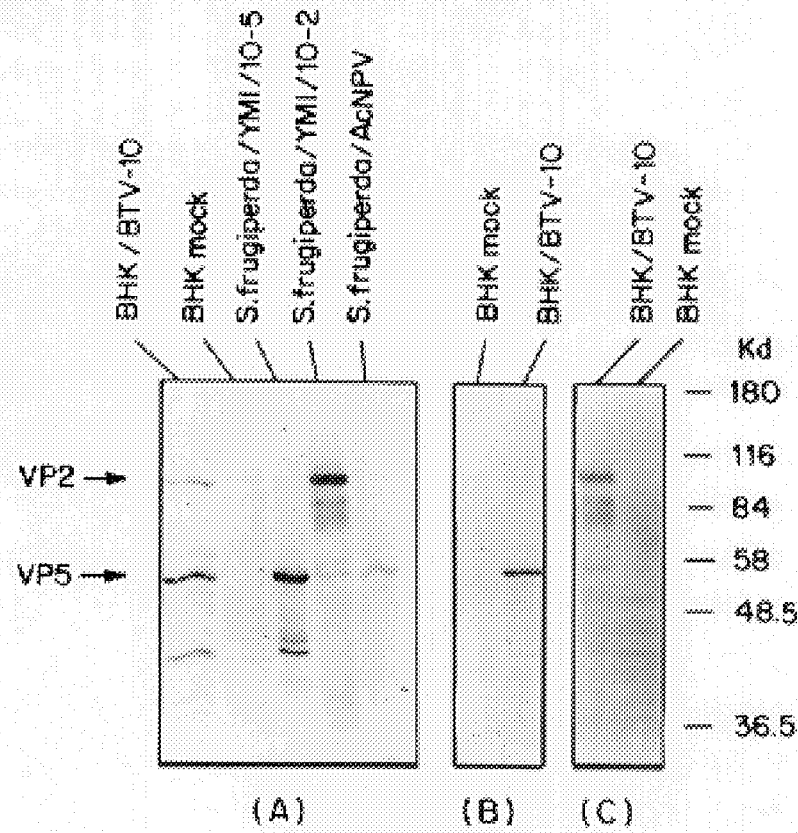
FIGS. 5 (A, B and C) Immunoblotting of expressed and authentic BTV proteins. Protein extracts of S. frugiperda cells infected with YM1/10-5, YM1/10-2 or AcNPV and BHK cells mock and BTV-10 infected were resolved by 10% SDS-PAGE and electrophoretically blotted as described in Methods. In (a) the membrane was probed with rabbit sera raised to BTV-10 virions. In (b) the membrane was probed with mouse ascitic fluid raised to expressed VP5 and in (c) the membrane was probed with rabbit sera raised to expressed VP2. The positions of the VP2 and VP5 proteins are indicated as well as those of molecular weight markers.
Figure 6A:
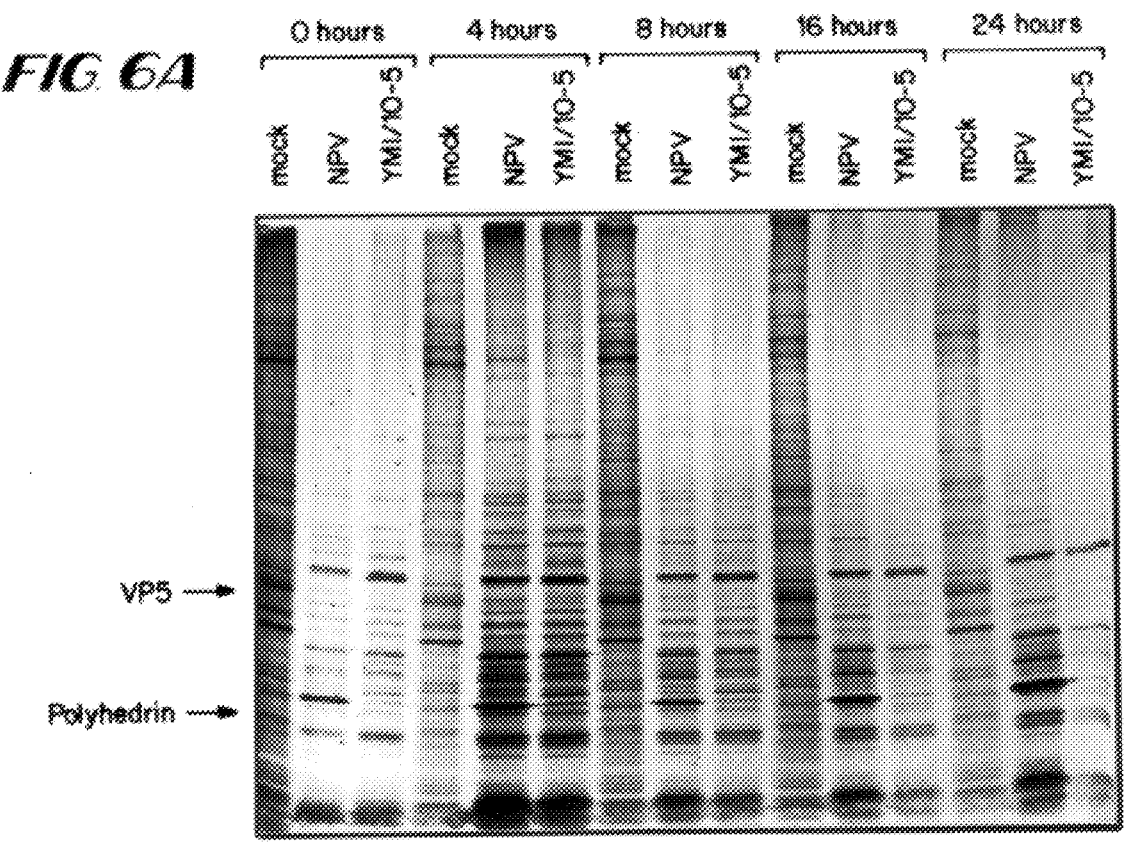
FIGS. 6A and 6B Pulse-chase [$^{35}$S]-methionine labelling time course of S. frugiperda cells either mock, AcNPV (NPV) or YM1/10-5 infected for 24 hours. After labelling the cells were chased for 0, 4, 8, 16 and 24 hours as described in Methods. Protein extracts were then resolved by SDS-PAGE and autoradiography either untreated (a) or after immune precipitation with rabbit anti BTV-10 antisera (b). The positions of VP5 and polyhedrin proteins as well as molecular weight markers and indicated.
Figure 6B:
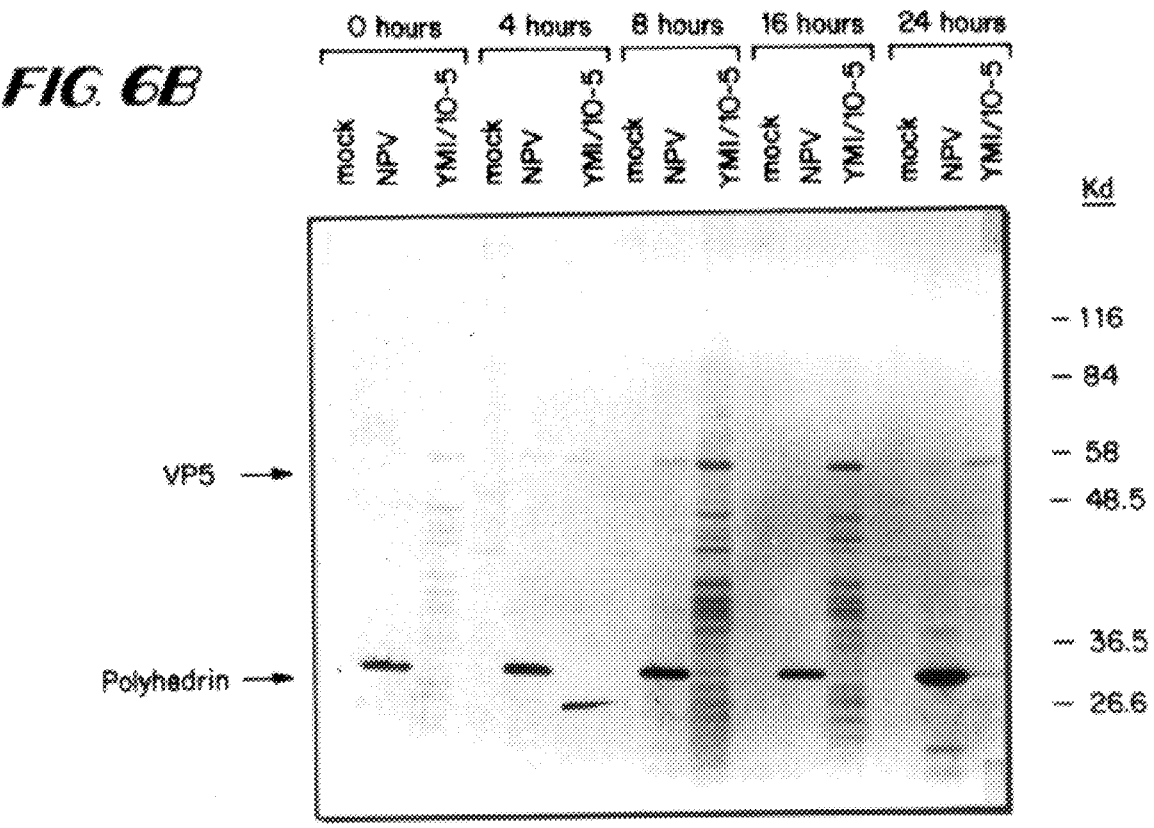
Figure 7:
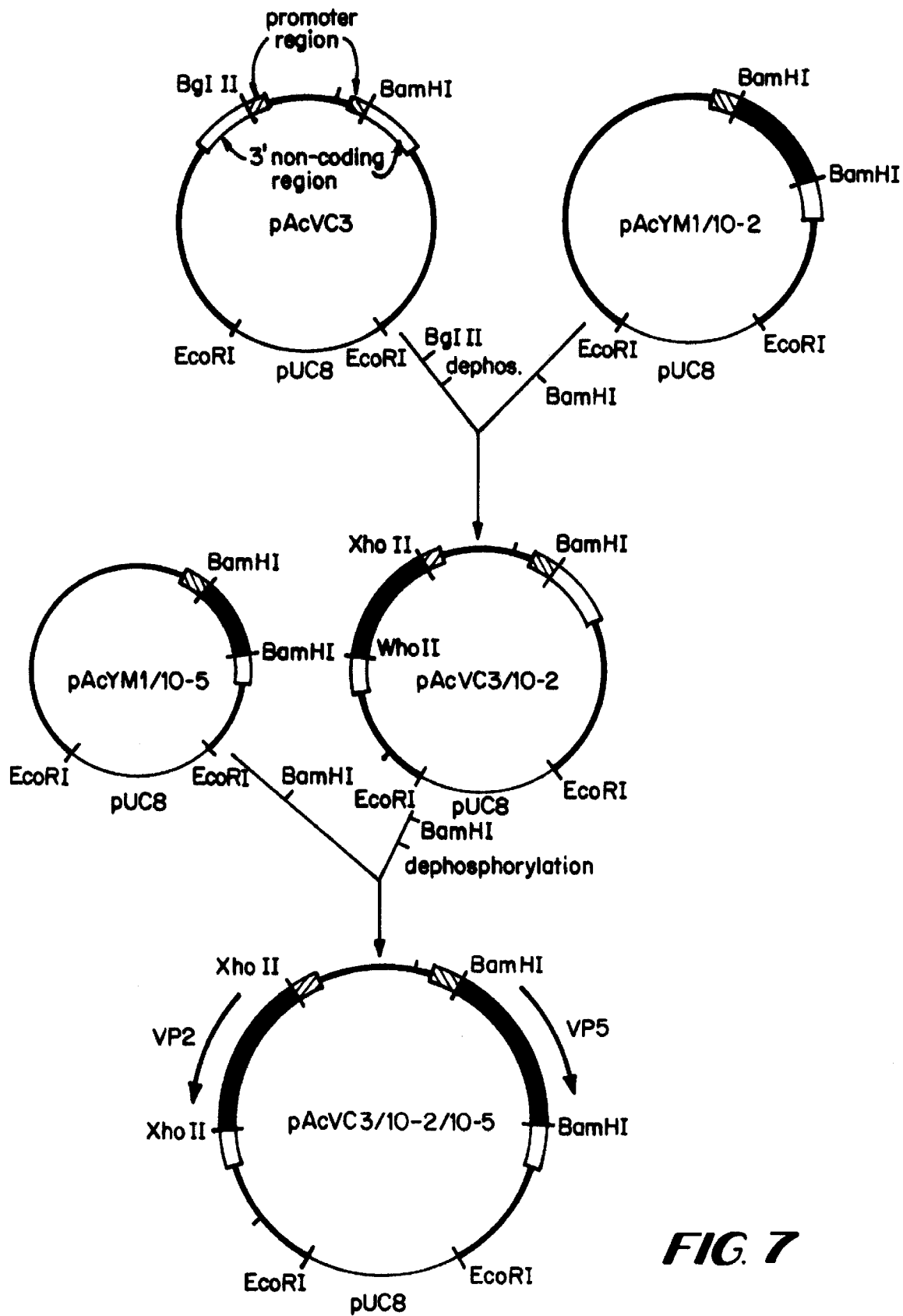
FIG. 7 Construction of the baculovirus expression transfer vector containing the L2 and M5 genes of BTV serotype 10. The cloning, genetic manipulations, and individual expression of these genes have previously been described. The L2 and M5 genes were excised from their single baculovirus expression transfer vector (pAcYM1) and ligated into the BglII and BamHI sites respectively of the multiple expression vector pAcVC3.
Figure 8A:
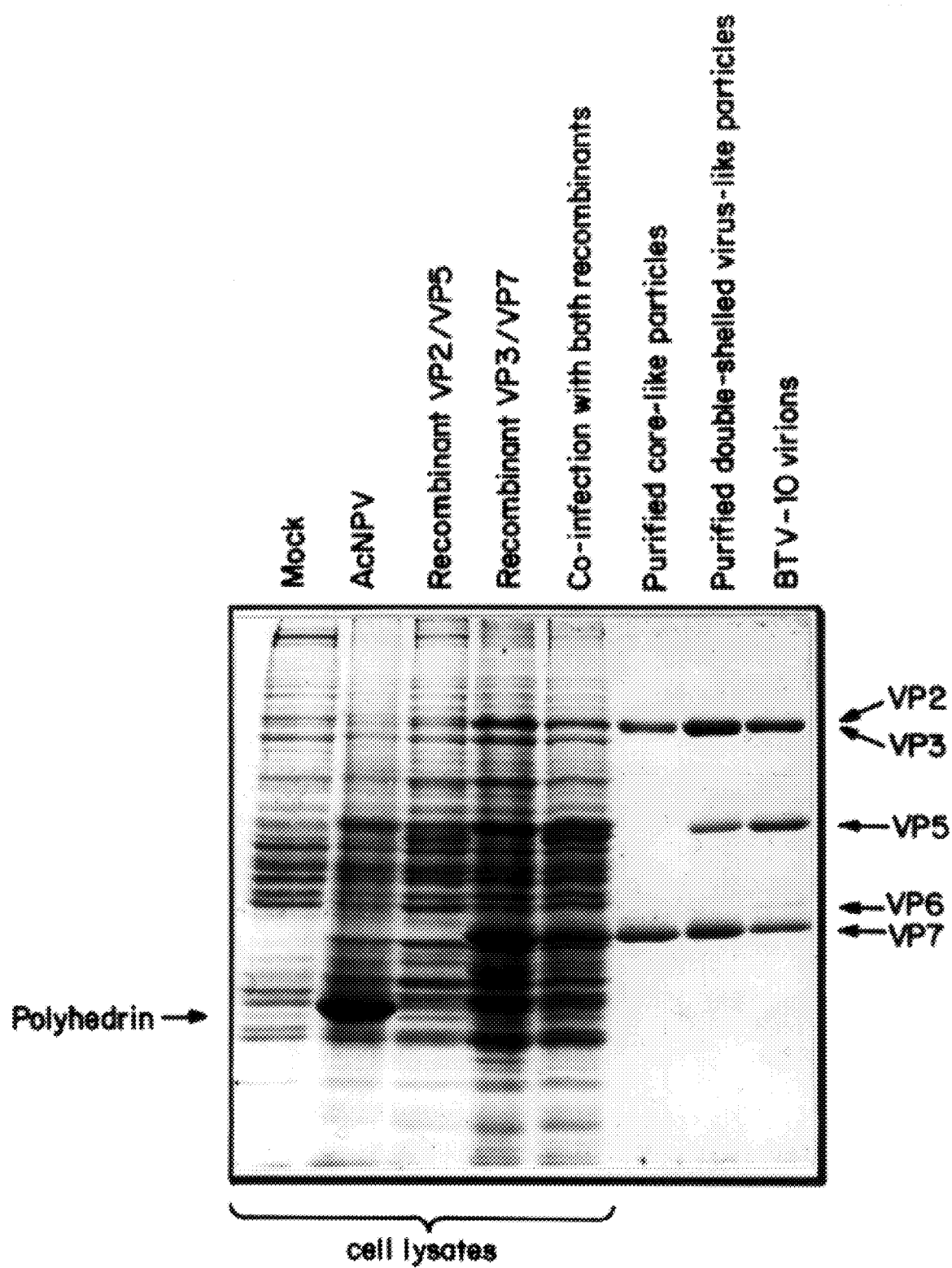
FIGS. 8A, 8B and 8C. Expression of the four major BTV structural proteins VP2, VP3, VP5 and VP7 in insect cells by recombinant baculoviruses, and confirmation of their authenticity by Western Immunoblot analysis. S. frugiperda cells were infected at a multiplicity of 5 pfu/cell with either the recombinant baculovirus expressing VP2 and VP5, or the recombinant expressing VP3 and VP7, or were co-infected with both recombinant viruses. Mock and wild-type AcNPV infected cells acted as controls. Cells were harvested at 48 h post-infection, washed with PBS and lysed at 4° C. in 50 mM Tris-HCl pH 8.0, 150 mM NaCl, 0.5% NP40. The expressed particles (both single-shelled core-like particles and double-shelled virus-like particles) were purified by banding at the interface of a 30% w/v, and 66% w/v discontinuous sucrose gradient (in 0.2M Tris-HCl, pH 8.0) after centrifugation at 85,000 g for 3 h. Authentic BTV virions prepared from BTV-infected BHK cells are included for comparison. Proteins were separated by SDS-PAGE and stained with Coomassie Blue (A), or were electroblotted onto Immobilon membrane and reacted with rabbit BTV-10 antiserum (B). Since VP2 co-migrates with VP3, its presence in the purified double-shelled virus-like particles and authentic. BTV virions was confirmed by reacting with antisera raised to expressed VP2 (C). Bound antibody was detected with an alkaline phosphatase conjugate using standard methods.
Figure 8B:
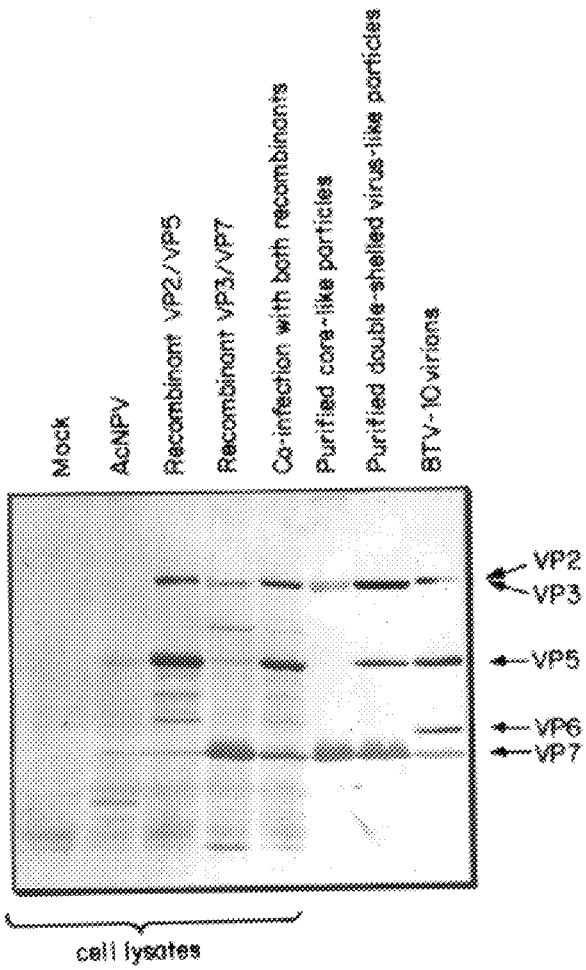
Figure 8C:
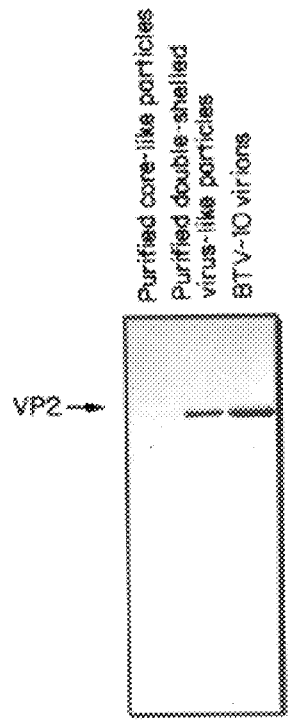
Figure 10:
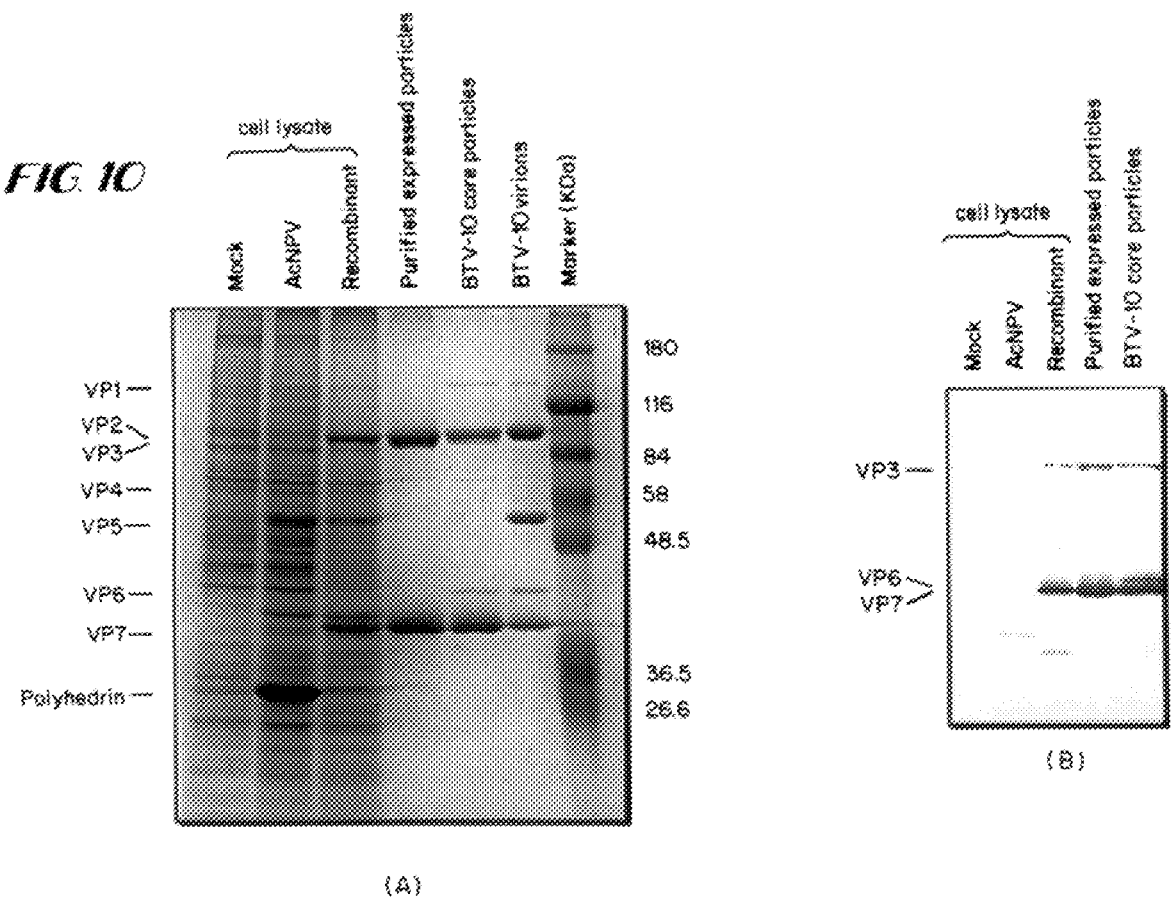
FIGS. 10 (A and B). Expression of the BTV core proteins VP3 and VP7 in insect cells by the recombinant baculovirus, and confirmation of their authenticity by Western blot analysis. S. frugiperda cells were infected at a multiplicity of 10 pfu/cell with recombinant virus, wild-type AcNPV, or were mock infected. Cells were harvested at 48 h post-infection, washed with PBS and lysed at 4° C. in 50 mM Tris-Hcl pH 8.0, 150 mM NaCl, 0.5% NP40. The expressed particles were purified by banding at the interface of a 30% w/v, 50% w/v discontinuous sucrose gradient (in 0.2M Tris-HCl pH 8.0) after centrifugation at 85,000 rpm for 3 h. Authentic BTV virions and core particles prepared from BTV-infected BHK cells are included for comparison. Proteins were separated by SDS-PAGE and stained with Coomassie blue (A), or were electroblotted onto immobilon membrane, and reacted with rabbit anti BTV-10 serum (B). Bound antibody was detected with an alkaline phosphatase conjugate by the standard method.
Figure 11B:
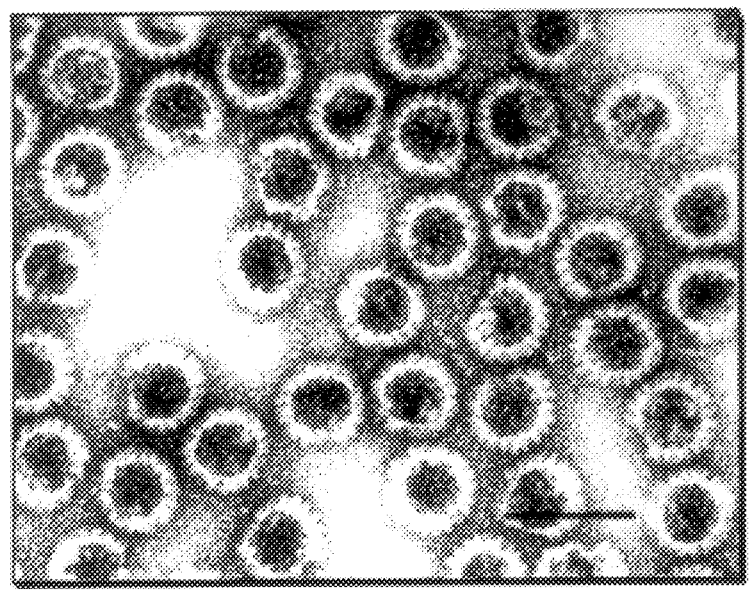
Figure 11C:
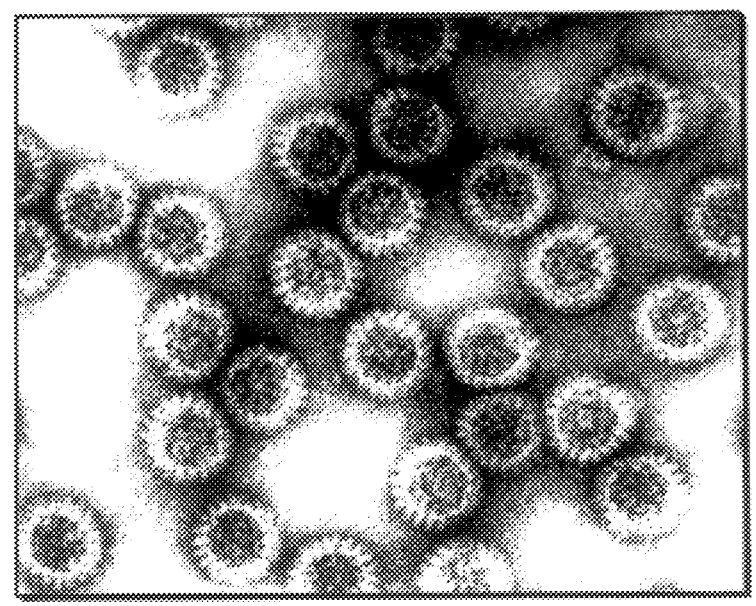
Figure 12A:
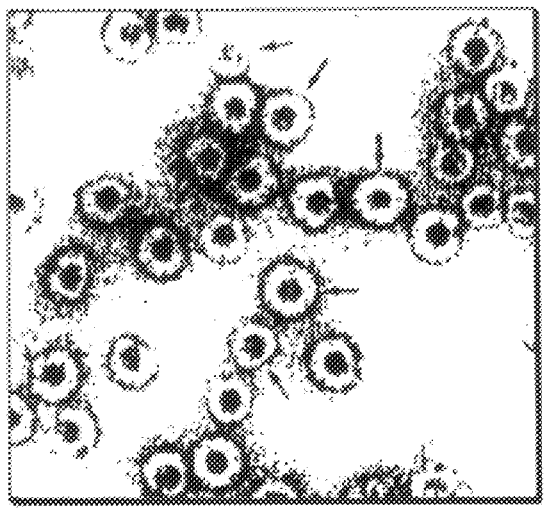
FIGS. 12A, 12B, 12C and 12D. Electron micrographs of baculovirus expressed particles. Empty BTV double-shelled virus-like particles are shown in (A) compared with authentic BTV particles (B). The high magnification micrographs (×30,000) show the appearance of expressed core-like particles composed of VP3 and VP7 (C), and the double-shelled particles with VP2 and VP5 attached to VP3 and VP7 (D).
Figure 12B:
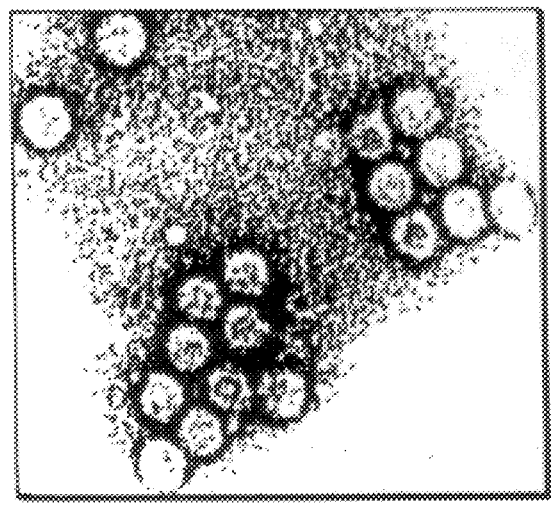
Figure 12C:
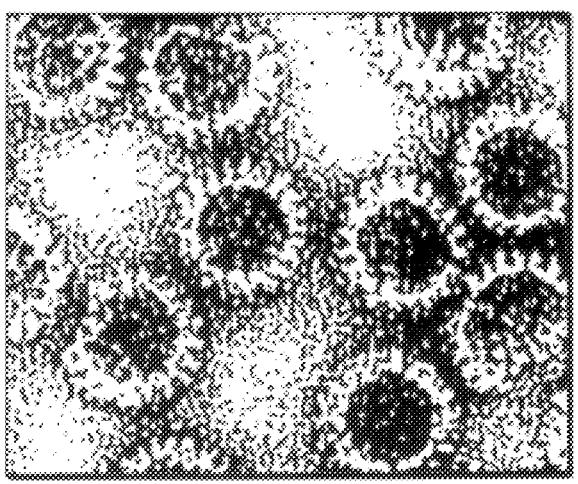
Figure 12D:
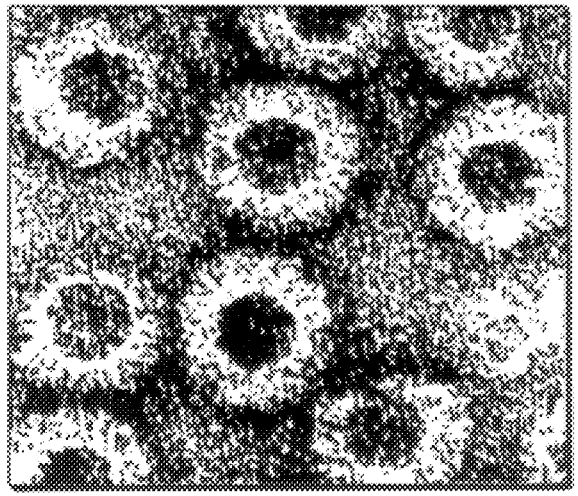

We claim:

1. A method of obtaining a protective effect against bluetongue infection in a susceptible mammal, which comprises inoculating said mammal with a polypeptide comprising bluetongue virus structural protein VP2 and bluetongue virus structural protein VP5 produced by a single host cell transformed with a recombinant baculovirus expression vector comprising a DNA segment coding for said structural protein VP2 and a DNA segment coding for said structural protein VP5.

2. A method according to claim 1, wherein said susceptible mammal is a ruminant.

3. A method according to claim 1, wherein said structural protein VP2 and said structural protein VP5 are co-expressed with an additional bluetongue virus structural protein selected from the group consisting of bluetongue virus structural protein VP3 and bluetongue structural virus protein VP7.

4. A vaccine composition comprising a polypeptide comprising bluetongue virus structural protein VP2 and bluetongue virus structural protein VP5 produced by a procedure as defined in claim 1.

5. A vaccine according to claim 4, and additionally comprising a polypeptide selected from the group consisting of bluetongue virus structural protein VP3 and bluetongue virus structural protein VP7.

* * * * *